US008662624B2

(12) United States Patent
Sato (10) Patent No.: US 8,662,624 B2
(45) Date of Patent: Mar. 4, 2014

(54) FOREIGN OBJECT DETECTION DEVICE, FOREIGN OBJECT DETECTION METHOD, DROPLET DISCHARGING DEVICE, AND DROPLET DISCHARGING METHOD

(75) Inventor: Tsuyoshi Sato, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 208 days.

(21) Appl. No.: 13/315,803

(22) Filed: Dec. 9, 2011

(65) Prior Publication Data

US 2012/0147081 A1 Jun. 14, 2012

(30) Foreign Application Priority Data

Dec. 9, 2010 (JP) ................................ 2010-275033
Feb. 25, 2011 (JP) ................................ 2011-039540

(51) Int. Cl.
*B41J 29/393* (2006.01)
(52) U.S. Cl.
USPC ............................................................ 347/19
(58) Field of Classification Search
CPC .......................... B41J 2/0451; B41J 2/04581
USPC ............. 347/19, 75, 84, 85, 92, 94; 73/61.75
See application file for complete search history.

(56) References Cited

U.S. PATENT DOCUMENTS

| 4,220,040 | A | * | 9/1980 | Noguchi et al. ............. 73/24.01 |
| 6,257,694 | B1 | | 7/2001 | Tokumaru et al. |
| 8,136,900 | B2 | * | 3/2012 | Iwasaki et al. .................... 347/5 |

FOREIGN PATENT DOCUMENTS

| JP | 4-158258 | A | 6/1992 |
| JP | 10-90236 | A | 4/1998 |
| JP | 2000-258281 | A | 9/2000 |
| JP | 2001-199061 | | 7/2001 |
| JP | 2001-199061 | A | 7/2001 |
| JP | 2002-236111 | A | 8/2002 |
| JP | 2002-303608 | A | 10/2002 |
| JP | 2003-14703 | | 1/2003 |
| JP | 2005-211873 | | 8/2005 |
| JP | 2006-26584 | A | 2/2006 |
| JP | 2007-513341 | A | 5/2007 |
| JP | 2007-155458 | A | 6/2007 |
| JP | 2007-322139 | A | 12/2007 |
| JP | 2009-72696 | A | 4/2009 |

OTHER PUBLICATIONS

Korean Office Action issued May 20, 2013, in Korea Patent Application No. 10-2011-130869 (with English translation).

(Continued)

*Primary Examiner* — An Do
(74) *Attorney, Agent, or Firm* — Oblon, Spivak, McClelland, Maier & Neustadt, L.L.P.

(57) ABSTRACT

According to one embodiment, a foreign object detection device includes a signal generator, a transmitter, a receiver, a storage section, and a detection section. A signal generator configured to generate an electrical signal. A transmitter configured to convert the electrical signal from the signal generator and to generate a pressure wave in a liquid. A receiver configured to receive a reflection wave from the liquid and to convert it to an electrical signal. A storage section configured to store information on a state of absence of a foreign object in the liquid. A detection section configured to detect at least one of presence or absence of the foreign object and size of the foreign object based on difference between the electrical signal converted from the reflection wave and an electrical signal based on the stored information.

18 Claims, 5 Drawing Sheets

(56) References Cited

OTHER PUBLICATIONS

Office Action issued Dec. 6, 2012 in Japanese Patent Application No. 2011-039540 with English language translation.

Office Action issued Aug. 12, 2013 in Japanese Patent Application No. 2011-039540 with English language translation.

Tsuyoshi Sato, et al., "Study on Detection Technique for Jetting Failure of Piezo-Driven Inkjet Heads", The Japan Society for Precision Engineering Meeting Abstracts, Aug. 25, 2009, pp. 867-868.

* cited by examiner

FOREIGN OBJECT DETECTION DEVICE, FOREIGN OBJECT DETECTION METHOD, DROPLET DISCHARGING DEVICE, AND DROPLET DISCHARGING METHOD

CROSS-REFERENCE TO RELATED APPLICATIONS

This application is based upon and claims the benefit of priority from the prior Japanese Patent Application No. 2010-275033, filed on Dec. 9, 2010 and the prior Japanese Patent Application No. 2011-039540, filed on Feb. 25, 2011; the entire contents of which are incorporated herein by reference.

FIELD

Embodiments described herein relate generally to a foreign object detection device, foreign object detection method, droplet discharging device, and droplet discharging method.

BACKGROUND

There are known techniques for detecting foreign objects in a liquid.

For instance, in the field of droplet discharging devices, there are proposals of techniques for detecting whether a bubble or other foreign object exists in the liquid to be discharged.

In such techniques, the presence or absence of a bubble is determined from e.g. the attenuation of the vibration level due to the existence of a bubble and the residual vibration waveform.

However, in such techniques, it is difficult to detect a bubble or other foreign object in a small region such as a thin duct. Thus, there is demand for the development of techniques capable of accurately detecting a bubble or other foreign object in a small region such as a thin duct.

DETAILED DESCRIPTION

In general, according to one embodiment, a foreign object detection device includes a signal generator, a transmitter, a receiver, a storage section, and a detection section. A signal generator configured to generate an electrical signal. A transmitter configured to convert the electrical signal from the signal generator and to generate a pressure wave in a liquid. A receiver configured to receive a reflection wave from the liquid and to convert it to an electrical signal. A storage section configured to store information on a state of absence of a foreign object in the liquid. A detection section configured to detect at least one of presence or absence of the foreign object and size of the foreign object based on difference between the electrical signal converted from the reflection wave and an electrical signal based on the stored information.

Embodiments will now be illustrated with reference to the drawings. In the drawings, similar components are labeled with like reference numerals, and the detailed description thereof is omitted appropriately.

By way of example, the following describes the case where a foreign object detection device is provided in a droplet discharging device, and the case where a foreign object detection method is applied to a droplet discharging method. However, applications of the foreign object detection device and the foreign object detection method are not limited thereto, but can be widely applied to detection of a bubble or other foreign object contained in a liquid.

First Embodiment

Figure 1:
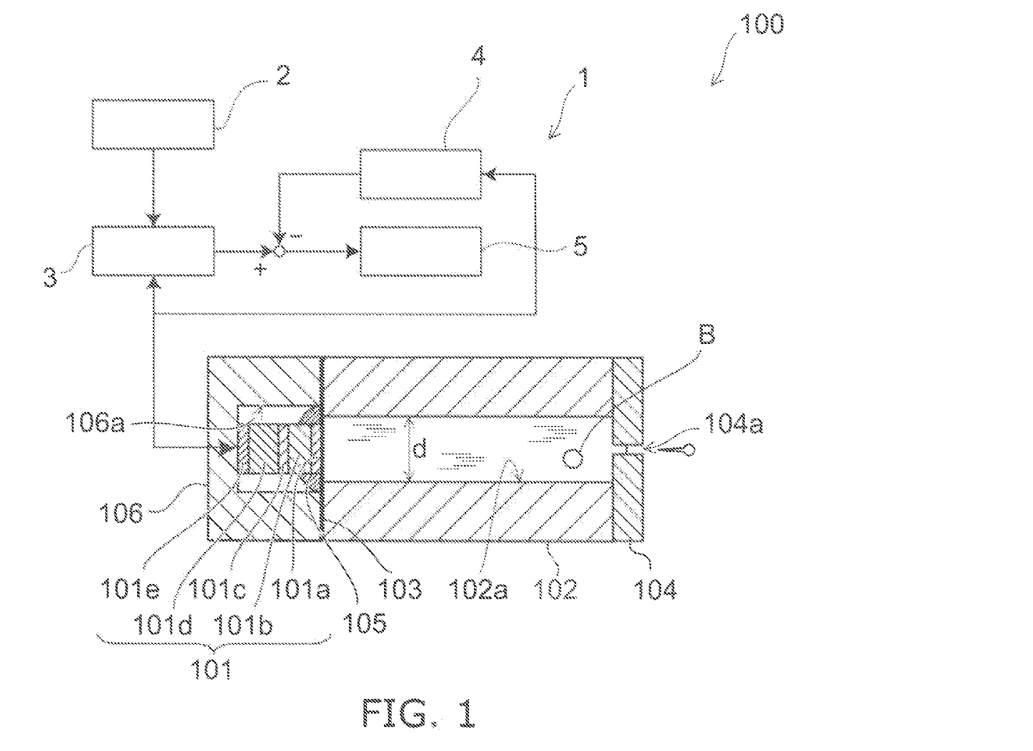
FIG. 1 is a schematic view for illustrating a foreign object detection device and a droplet discharging device according to a first embodiment.

FIG. 1 is a schematic view for illustrating a foreign object detection device and a droplet discharging device according to a first embodiment.

Driving systems for droplet discharging devices include the "thermal type" system for discharging liquid based on the film boiling phenomenon of a bubble generated by heating, and the "piezoelectric type" system for discharging liquid based on the bending displacement of a piezoelectric element. In the following description, the piezoelectric type is taken as an example.

The droplet discharging device 100 includes a piezoelectric section 101, a nozzle body 102, a flexible film 103, a nozzle section 104, an attenuator 105, a cover 106, and a foreign object detection device 1.

The piezoelectric section 101 can be made of e.g. a driving electrode 101a, a member 101b, a driving electrode 101c, a member 101d, and a driving electrode 101e, which are sequentially stacked and then integrally sintered. The integrally sintered piezoelectric section 101 has high strength and is easy to handle.

The member 101b and the member 101d can be formed from a piezoelectric material. Examples of the piezoelectric material can include piezoelectric ceramics (e.g., lead zirconate titanate). The driving electrode 101a, the driving electrode 101c, and the driving electrode 101e can be formed from e.g. copper alloy.

As described later, the piezoelectric section 101 serves as a pressurization source for discharging liquid. At the same time, the piezoelectric section 101 also has the function of a transmitter and a receiver of the foreign object detection device 1. The signal generator 2 provided in the foreign object detection device 1 also has the function of outputting an electrical signal for driving the piezoelectric section 101 as a pressurization source.

The nozzle body 102 includes a liquid chamber 102a for containing liquid to be discharged. The liquid chamber 102a is provided so as to penetrate between both end portions of the nozzle body 102. For instance, the liquid chamber 102a can have a cross section with an equivalent diameter dimension of d.

Here, in the case where the cross-sectional shape of the liquid chamber 102a is a circle, the equivalent diameter dimension d is the diameter dimension of the circle. In the case where the cross-sectional shape of the liquid chamber 102a is e.g. a polygon, the cross section is converted to a circle having the same cross-sectional area, and the equivalent diameter dimension d is the diameter dimension of the circle.

The details of the equivalent diameter dimension d will be described later.

The liquid chamber 102a is in communication with a flow channel, not shown, so that liquid is supplied into the liquid chamber 102a via the flow channel, not shown.

The nozzle body 102 can be formed from e.g. stainless steel or nickel alloy.

The flexible film 103 is provided on one end portion of the nozzle body 102. The flexible film 103 is provided so as to cover the opening of the liquid chamber 102a.

On the surface of the flexible film 103 on the opposite side from the side provided on the nozzle body 102, the piezoelectric section 101 is provided. In this case, the piezoelectric section 101 can be opposed to the opening of the liquid chamber 102a so that the pressure wave resulting from the bending displacement of the piezoelectric section 101 is easily transmitted to the liquid in the liquid chamber 102a. In this embodiment, the piezoelectric section 101 serves as a pressurizer for pressurizing the liquid in the liquid chamber 102a provided on one end portion side of the nozzle body 102.

The flexible film 103 can be formed from e.g. stainless steel.

The nozzle section 104 is provided on the other end portion of the nozzle body 102. The nozzle section 104 is shaped like a plate and includes a nozzle hole 104a penetrating in the thickness direction. One end of the nozzle hole 104a is opened into the liquid chamber 102a, and the other end is opened to the outside of the droplet discharging device 100.

The nozzle section 104 can be formed from e.g. stainless steel or nickel alloy.

The attenuator 105 is provided on the flexible film 103 so as to surround the periphery of the piezoelectric section 101. In the piezoelectric section 101, the so-called main vibration occurs. At the same time, unwanted vibrations such as spurious vibrations also occur. Thus, the attenuator 105 is provided to attenuate e.g. spurious vibrations to reduce adverse effects of e.g. spurious vibrations on the main vibration.

The attenuator 105 can be formed from e.g. silicone rubber.

The cover 106 includes a recess 106a with one end opened. The cover 106 is provided on the flexible film 103 so as to house the piezoelectric section 101 and the attenuator 105 inside the recess 106a. Furthermore, the cover 106 appropriately includes e.g. holes, not shown, for threading wirings of the piezoelectric section 101.

The cover 106 can be formed from e.g. resin or metal.

The foreign object detection device 1 includes a signal generator 2, a switching section 3, a storage section 4, and a detection section 5.

As described above, in this embodiment, the piezoelectric section 101 serves the function of a transmitter for converting an electrical signal to generate a pressure wave in the liquid, and a receiver for receiving the reflection wave and converting it to an electrical signal.

Here, as described later, the reflection wave includes that based on mechanical vibrations, the "bubble-induced pressure wave", and the pressure wave generated by impingement on e.g. the wall of the liquid chamber 102a and the nozzle section 104. The details thereof will be described later.

The signal generator 2 generates an electrical signal for detecting a bubble B or other foreign object. More specifically, the signal generator 2 generates an electrical signal for causing the piezoelectric section 101 to generate a pressure wave having a prescribed frequency. In this case, the signal generator 2 can generate an electrical signal having a frequency f satisfying Equations (3) and (4) described later.

Here, it is also possible to provide a plurality of signal generators depending on the frequency range, and a switching section for the frequency range.

As described above, the signal generator 2 also has the function of outputting an electrical signal for driving the piezoelectric section 101 as a pressurization source.

The switching section 3 switches electrical signals. For instance, when the electrical signal from the signal generator 2 is sent to the piezoelectric section 101, the switching section 3 prevents the electrical signal from being sent to the detection section 5 side. On the other hand, when the electrical signal from the piezoelectric section 101 is sent to the detection section 5 side, the switching section 3 prevents the electrical signal from being sent to the signal generator 2 side.

The storage section 4 stores information serving as a reference. For instance, the storage section 4 can store information on the state of the absence of a bubble B or other foreign object in the liquid. The information on the state of the absence of a bubble B or other foreign object can be previously collected and stored. Furthermore, the information on the state of the absence of a bubble B or other foreign object can be estimated from e.g. the discharge state and successively stored.

The detection section 5 detects at least one of the presence or absence of a bubble B or other foreign object and the size of a bubble B or other foreign object based on the information collected by the piezoelectric section 101, i.e., the information on the reflection wave described later, and the information from the storage section 4. More specifically, the detection section 5 detects at least one of the presence or absence of a bubble B or other foreign object and the size of a bubble B or other foreign object based on the difference between the electrical signal converted from the reflection wave and the electrical signal based on the stored information.

In this case, as described later, the detection section 5 can detect the size of a foreign object based on the square of the difference between the electrical signal converted from the reflection wave and the electrical signal based on the information stored in the storage section 4.

Alternatively, the detection section 5 can determine the scattering cross-sectional area σsc based on the difference between the electrical signal converted from the reflection wave and the electrical signal based on the information stored in the storage section 4. From the previously determined relationship between the size of a bubble B or other foreign object and the scattering cross-sectional area σsc, the detection section 5 can detect the size of a bubble B or other foreign object.

The detection section 5 can output the detection result on the presence or absence of a bubble B or other foreign object and the detection result of the size of a bubble B or other foreign object to e.g. external devices. The details of the detection of the presence or absence of a bubble B or other foreign object and the detection of the size of e.g. a bubble B will be described later.

Next, the operation of the foreign object detection device 1 is illustrated.

In the following description, the case where the foreign object is a bubble B is taken as an example.

Figure 2:
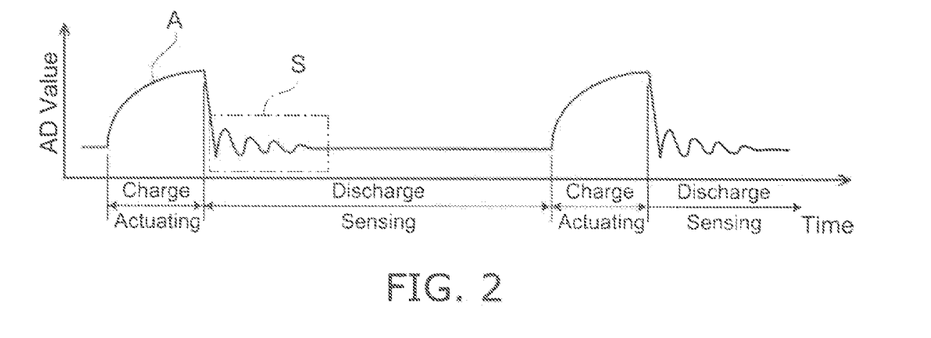
FIG. 2 is a schematic graph for illustrating the timing of detection.

FIG. 2 is a schematic graph for illustrating the timing of detection.

As shown in FIG. 2, upon application of a prescribed electrical signal A to the piezoelectric section 101, a pressure wave is generated in the liquid.

After the application of the electrical signal A, for instance, as a result of mechanical vibrations by e.g. the flexible film 103, the "bubble-induced pressure wave" described later, and the pressure wave generated by impingement on e.g. the wall of the liquid chamber 102a and the nozzle section 104, an electrical signal as represented by S in FIG. 2 is detected by the piezoelectric section 101 also serving as a receiver.

Thus, the detection of the presence or absence of a bubble B and the detection of the size of a bubble B are performed based on the electrical signal S.

Here, the electrical signal S also includes information other than the "bubble-induced pressure wave". However, the information other than the "bubble-induced pressure wave" can be removed by determining the difference from the electrical signal for the absence a bubble B in the detection section 5.

First, for detection regarding a bubble B, an electrical signal having a prescribed frequency f is generated in the signal generator 2. This electrical signal is intended to cause the piezoelectric section 101 to generate a pressure wave having a prescribed frequency.

In the case where a plurality of signal generators depending on the frequency range and a switching section for the frequency range are provided, the frequency range is switched so as to be able to generate an electrical signal having an appropriate frequency.

The details of the frequency f will be described later.

The electrical signal outputted from the signal generator 2 is inputted to the piezoelectric section 101 via the switching section 3. The piezoelectric section 101 also serving as a transmitter of the foreign object detection device 1 generates a pressure wave by converting the inputted electrical signal to a bending displacement.

The generated pressure wave propagates in the liquid in the liquid chamber 102a via the flexible film 103 and impinges on e.g. the wall of the liquid chamber 102a and the nozzle section 104. This generates a pressure wave due to scattering (reflection). In the presence of a bubble B, the pressure wave impinges on the bubble B, generating a pressure wave due to scattering (reflection). Furthermore, by impingement of the pressure wave on the bubble B, the bubble B undergoes volume change, generating a pressure wave resulting from this volume change. Here, the pressure wave resulting from the volume change is incomparably higher in pressure than the pressure wave due to scattering by the bubble B.

In this specification, the pressure wave due to scattering by impingement on the bubble B and the pressure wave resulting from the volume change of the bubble B are collectively referred to as "bubble-induced pressure wave".

Furthermore, the "bubble-induced pressure wave", the pressure wave generated by impingement on e.g. the wall of the liquid chamber 102a and the nozzle section 104, and those related to mechanical vibrations of e.g. the flexible film 103 described above, are collectively referred to as "reflection wave".

Thus, the reflection wave includes information on a bubble B, such as the presence or absence and the size of a bubble B.

The generated reflection wave is incident on the piezoelectric section 101 also serving as a receiver of the foreign object detection device 1, and converted to an electrical signal corresponding to the bending displacement of the piezoelectric section 101.

The electrical signal based on the reflection wave is inputted to the detection section 5 via the switching section 3. On the other hand, from the storage section 4, information on the state of the absence of a bubble B is converted to an electrical signal and provided. Then, the detection section 5 determines the difference between the electrical signal based on the reflection wave and the electrical signal for the absence of a bubble B to extract information on a bubble B.

The detection section 5 detects the presence or absence of a bubble B based on the extracted information on a bubble B. The detection of the presence or absence of a bubble B can be performed based on e.g. a predetermined threshold. Furthermore, the detection section 5 can also detect the size of a bubble B based on the extracted information on a bubble B.

Next, the detection of the presence or absence of a bubble B and the detection of the size of a bubble B are further illustrated.

Figure 3A:
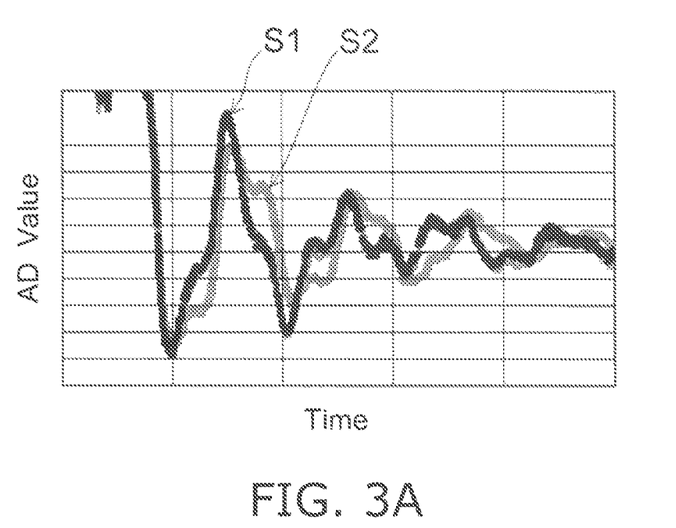
FIG. 3A is a schematic graph for illustrating an electrical signal S1 based on the reflection wave in the presence of a bubble B, and an electrical signal S2 based on the reflection wave in the absence of a bubble B.
Figure 3B:
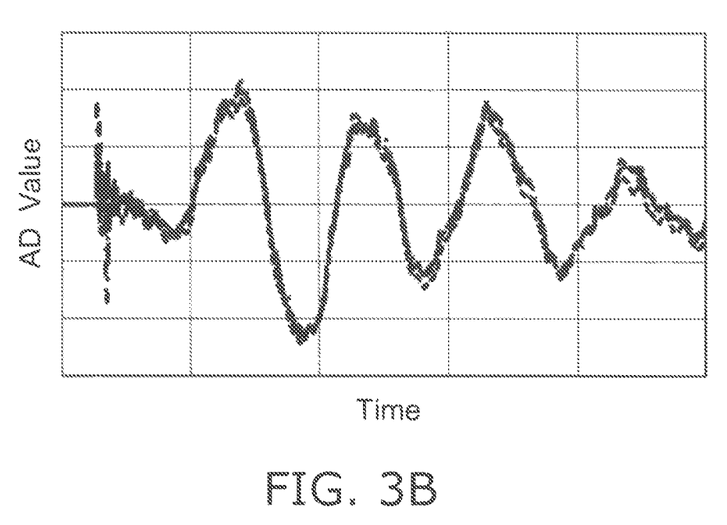
FIG. 3B is a schematic graph for illustrating an electrical signal including information on a bubble B.

FIGS. 3A and 3B are schematic graphs for illustrating the extraction of information on a bubble B.

More specifically, FIG. 3A is a schematic graph for illustrating an electrical signal S1 based on the reflection wave in the presence of a bubble B, and an electrical signal S2 based on the reflection wave in the absence of a bubble B. FIG. 3B is a schematic graph for illustrating an electrical signal including information on a bubble B.

As shown in FIG. 3A, the electrical signal S1 based on the reflection wave in the presence of a bubble B and the electrical signal S2 in the absence of a bubble B are different in waveform.

Hence, by determining the difference between the electrical signal S1 based on the reflection wave in the presence of a bubble B and the electrical signal S2 in the absence of a bubble B, an electrical signal including information on a bubble B can be extracted as shown in FIG. 3B. Here, the electrical signal based on the reflection wave in the absence of a bubble B and the electrical signal S2 in the absence of a bubble B are similar in waveform. Hence, the difference therebetween is determined to be nearly 0 (zero).

The presence or absence of a bubble B can be detected by using the information on a bubble B thus extracted and e.g. a predetermined threshold.

Figure 4:
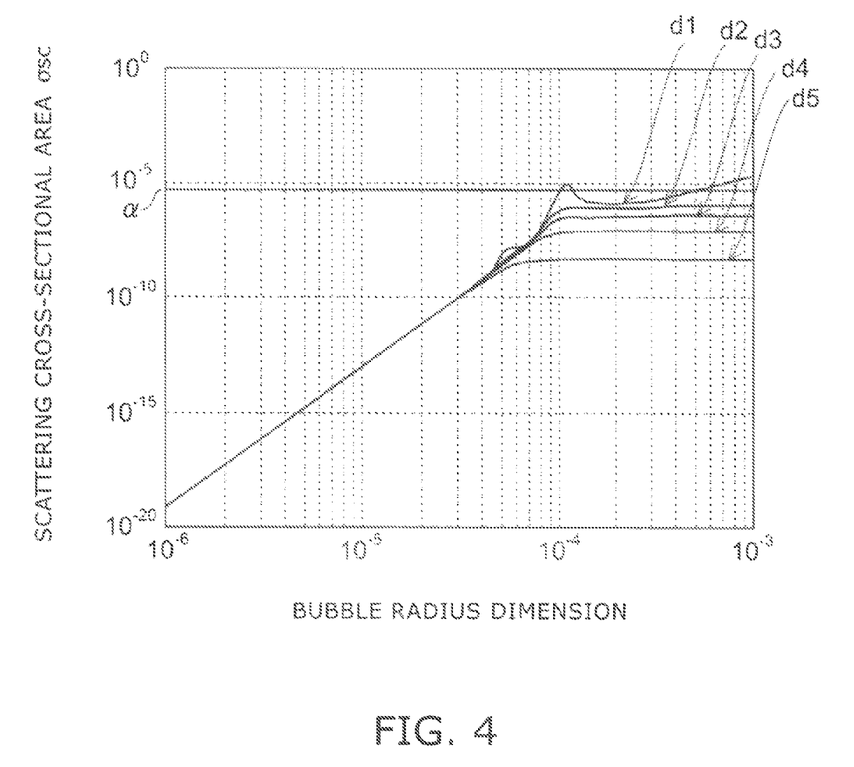
FIG. 4 is a graph for illustrating the relationship between the radius dimension of a bubble B and the scattering cross-sectional area.

FIG. 4 is a graph for illustrating the relationship between the radius dimension of a bubble B and the scattering cross-sectional area.

The horizontal axis represents the radius dimension of a bubble B, and the vertical axis represents the scattering cross-sectional area σsc. In this figure, d1-d5 represent the equivalent diameter dimension of the liquid chamber 102a. Here, d1, d2, d3, d4, and d5 represent the case of 10 mm, 4 mm, 3 mm, 2 mm, and 1 mm, respectively.

In the relationship between the radius dimension of a bubble B and the scattering cross-sectional area σsc, even if the scattering cross-sectional area σsc is fixed, there may be a plurality of radius dimensions of a bubble B corresponding to the scattering cross-sectional area σsc.

For instance, as shown in FIG. 4, consider the case where the equivalent diameter dimension is d1. If the scattering cross-sectional area σsc is set to α, there are three radius dimensions of a bubble B corresponding thereto.

Thus, in such a case, it is difficult to determine the size of the bubble B.

In this case, conventionally, the size of the bubble B cannot be determined. Hence, it is impossible to take measures such as ejection operation before the bubble B grows to a size causing discharge anomaly (such as occurrence of non-discharge, degradation of uniformity in the amount of liquid, and degradation of shooting accuracy). Thus, occurrence of discharge anomaly cannot be prevented.

However, as shown in FIG. 4, in the linear portion of the relationship between the radius dimension of a bubble B and the scattering cross-sectional area σsc, the radius dimension of a bubble B can be determined from the scattering cross-sectional area σsc. Here, the scattering cross-sectional area σsc can be determined by the following Equation (1).

[Equation 1]

$$\sigma sc = \frac{Wsc}{Iinc} \quad (1)$$

Here, Wsc is the scattering power, and Iinc is the incident intensity.

The scattering power Wsc can be determined by the following Equation (2).

[Equation 2]

$$Wsc = \frac{4\pi}{\rho c} \langle r^2 Ps(r, t)^2 \rangle_t \quad (2)$$

Here, ρ is the density of the liquid, c is the speed of sound, r is the distance to the bubble B, and Ps(r, t) is the pressure emitted from the bubble B. In this case, Ps(r, t) has space dependence and time dependence. Furthermore, $\langle \rangle_t$ represents time average. In a small region, r can be set to the dimension in the pressure propagation direction of the component containing the liquid. For instance, for the liquid chamber 102a, r can be set to the axial dimension (the dimension in the discharge direction) of the liquid chamber 102a.

Because Ps(r, t) represents the pressure emitted from the bubble B, the waveform illustrated in FIG. 3B yields Ps(r, t).

That is, by extracting an electrical signal including information on a bubble B as illustrated in FIG. 3B, the scattering cross-sectional area σsc can be determined to detect the size of the bubble B.

Calculating the scattering cross-sectional area σsc from the electrical signal including information on a bubble B, and calculating the radius dimension of the bubble B from the calculated scattering cross-sectional area σsc, can be performed in the detection section 5.

Here, the case of calculating the radius dimension of the bubble B from the scattering cross-sectional area σsc has been illustrated. However, the embodiment is not limited thereto.

If Ps(r, t) including information on a bubble B can be known, the radius dimension of the bubble B can be calculated without calculating the scattering cross-sectional area σsc.

More specifically, in Equation (2), it is Ps(r, t) that includes information on a bubble B. Hence, like the relationship between the radius dimension of a bubble B and the scattering cross-sectional area σsc, the relationship between the radius dimension of a bubble B and Ps(r, t)² can be determined.

Thus, the size of a bubble B can be detected based on the square of the difference between the electrical signal including information on a bubble B and the electrical signal based on the information on the state of the absence of a bubble B.

Here, as shown in FIG. 4, the relationship between the radius dimension of a bubble B and the scattering cross-sectional area σsc includes a linear portion and a nonlinear portion.

Furthermore, it is found that the linear portion of the relationship between the radius dimension of a bubble B and the scattering cross-sectional area σsc is not significantly affected by the equivalent diameter dimension d1-d5 of the liquid chamber 102a.

Hence, the piezoelectric section 101 is preferably driven so that the relationship between the radius dimension of a bubble B and the scattering cross-sectional area σsc is linear.

In this case, if the driving frequency of the piezoelectric section 101, i.e., the frequency f of the electrical signal generated in the signal generator 2, is set as given by the following Equation (3), the relationship between the radius dimension of a bubble B and the scattering cross-sectional area σsc can be made linear.

[Equation 3]

$$f \approx \frac{1}{2\pi Ro} \sqrt{\frac{3\gamma Po}{\rho}} \quad (3)$$

Here, Ro is the maximum bubble size, Po is the equilibrium pressure of the liquid in the liquid chamber 102a, ρ is the density of the liquid, and γ is the specific heat ratio.

The maximum bubble size Ro is the radius dimension of the bubble that is the largest of the bubbles to be detected. For instance, the maximum bubble size Ro is the radius dimension of the bubble corresponding to the threshold used to determine the discharge anomaly described later.

In this case, the equilibrium pressure Po and the maximum bubble size Ro can be appropriately set depending on the target in which the foreign object detection device 1 is provided.

Then, for instance, the equilibrium pressure Po and the maximum bubble size Ro previously determined by e.g. experiment or simulation are used to determine the frequency f of the electrical signal to be generated in the signal generator 2. Then, by driving the piezoelectric section 101 with the determined frequency f, the relationship between the radius dimension of a bubble B and the scattering cross-sectional area σsc can be made linear. Thus, the radius dimension of a bubble B can be easily determined from the scattering cross-sectional area σsc calculated by using the above Equations (1) and (2).

That is, by driving the piezoelectric section 101 with the frequency f determined as described above, the radius dimension of a bubble B having a size equal to or less than the maximum bubble size Ro can be determined.

Furthermore, the equivalent diameter dimension d of the liquid chamber 102a can be taken into consideration to avoid the occurrence of a plurality of radius dimensions of a bubble B corresponding to the scattering cross-sectional area σsc.

That is, the number of radius dimensions of a bubble B corresponding to the scattering cross-sectional area σsc can be limited to one. This can eliminate false detection.

In this case, according to the knowledge obtained by the inventor, the occurrence of false detection can be eliminated by causing the signal generator 2 to generate an electrical signal having a frequency f satisfying the following Equation (4).

[Equation 4]

$$f \leq \frac{120}{d} \quad (4)$$

Here, d is the equivalent diameter dimension d of the liquid chamber 102a.

Alternatively, it is also possible to provide a liquid chamber 102a having an equivalent diameter dimension d satisfying the following Equation (5).

In this case, the liquid chamber 102a corresponds to an example of the container for containing liquid provided in the foreign object detection device 1.

[Equation 5]

$$d \leq \frac{120}{f} \quad (5)$$

Here, f is the frequency generated in the signal generator 2.

The information on the frequency f expressed in Equations (3) and (4) is inputted to the signal generator 2. The signal generator 2 generates an electrical signal based on the inputted information on the frequency f.

Alternatively, it is also possible to provide a calculation section, not shown, for calculating information on the frequency f based on inputs such as the maximum bubble size Ro, the equilibrium pressure Po of the liquid in the liquid chamber 102a, the density ρ of the liquid, the specific heat ratio γ, and the equivalent diameter dimension d of the liquid chamber 102a. Then, the calculated information on the frequency f can be provided from the calculation section, not shown, to the signal generator 2.

The foreign object detection device 1 according to this embodiment can detect not only the presence or absence of a bubble B or other foreign object, but also the size of a bubble B or other foreign object with high accuracy.

Thus, the prevention of trouble and the improvement of productivity can be achieved with higher reliability.

In the foregoing, the case of detecting the presence or absence of a bubble B has been illustrated. However, it is also possible to detect the presence or absence of dust or other solid foreign object. Furthermore, the case of detecting the size of a bubble B has been illustrated. However, it is possible to detect the size of a foreign object undergoing volume change by pressure change.

Next, the operation of the droplet discharging device 100 is illustrated.

In the signal generator 2, an electrical signal for causing the piezoelectric section 101 to generate a pressure wave is generated. In this case, the bending displacement, and hence the amount of discharge, of the piezoelectric section 101 can be controlled by controlling the voltage applied to the piezoelectric section 101. Thus, the electrical signal generated in the signal generator 2 has a voltage change corresponding to the amount of discharge.

The electrical signal outputted from the signal generator 2 is inputted to the piezoelectric section 101 via the switching section 3. The piezoelectric section 101 generates a pressure wave by converting the inputted electrical signal to a bending displacement. The generated pressure wave is transmitted to the liquid in the liquid chamber 102a via the flexible film 103. The liquid in the liquid chamber 102a is pressurized toward the nozzle hole 104a. The liquid pressurized toward the nozzle hole 104a is discharged as a droplet from the nozzle hole 104a. The amount of liquid decreased by the discharge is replenished into the liquid chamber 102a via a flow channel, not shown.

Then, for instance, the detection of the presence or absence of a bubble B and the detection of the size described above are performed successively or regularly.

Furthermore, based on the detected size of the bubble B, determination on the occurrence of discharge anomaly is made.

In this case, if there is a bubble B larger than a prescribed threshold, a maintenance operation for suspending the discharge operation and ejecting the bubble B from the liquid chamber 102a can be performed.

Furthermore, for instance, if the size of the bubble B is less than a prescribed threshold, the discharge operation can be continued. If the size of the bubble B is equal to or more than the prescribed threshold, a maintenance operation for suspending the discharge operation and ejecting the bubble B from the liquid chamber 102a can be performed.

The droplet discharging device 100 according to this embodiment can prevent the occurrence of trouble and improve the productivity.

Second Embodiment

Figure 5:
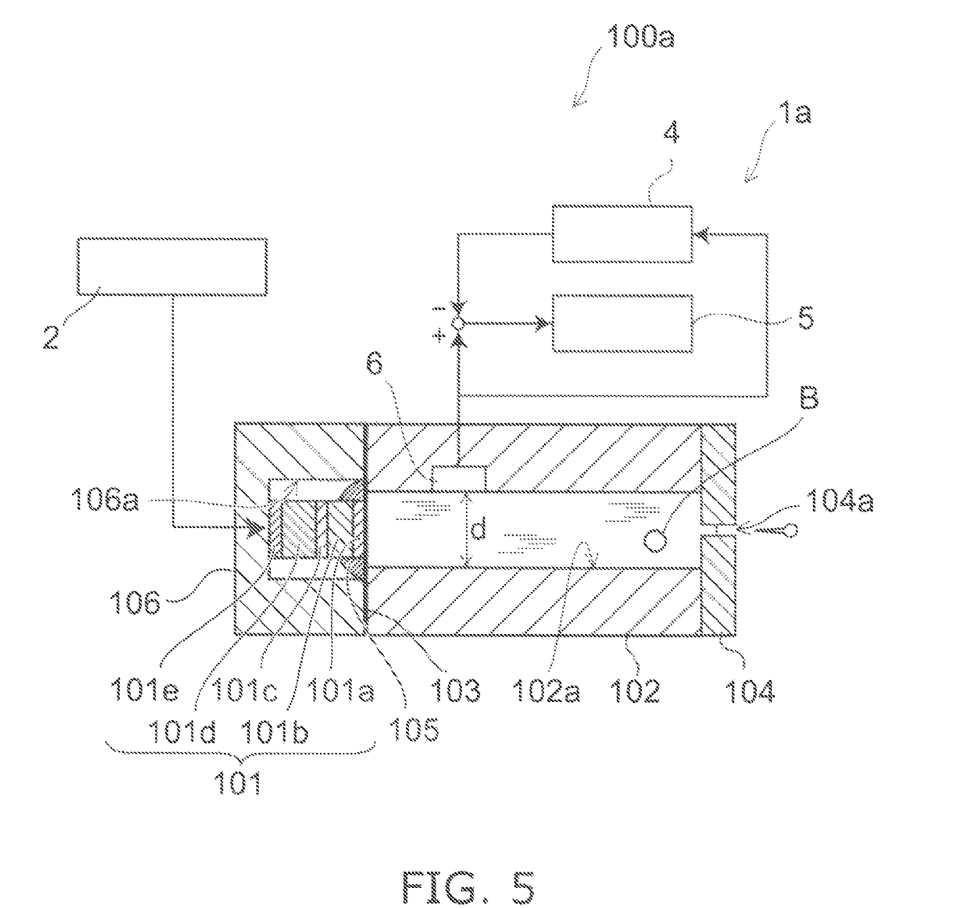
FIG. 5 is a schematic view for illustrating a foreign object detection device and a droplet discharging device according to a second embodiment.

FIG. 5 is a schematic view for illustrating a foreign object detection device and a droplet discharging device according to a second embodiment.

The droplet discharging device 100a illustrated in FIG. 5 is also a droplet discharging device of the piezoelectric type.

The droplet discharging device 100a includes a piezoelectric section 101, a nozzle body 102, a flexible film 103, a nozzle section 104, an attenuator 105, a cover 106, and a foreign object detection device 1a.

In this embodiment, the piezoelectric section 101 serves as a pressurization source for discharging liquid, and also has the function of a transmitter of the foreign object detection device 1a. However, unlike the droplet discharging device 100 described above, the piezoelectric section 101 does not have the function of a receiver of the foreign object detection device 1a.

The foreign object detection device 1a includes a signal generator 2, a storage section 4, a detection section 5, and a receiver 6.

In the foreign object detection device 1 described above, the piezoelectric section 101 is used as a transmitter and a receiver of the foreign object detection device 1, and switching of electrical signals is performed by the switching section 3.

In contrast, in the foreign object detection device 1a, the receiver 6 is separately provided. This eliminates the need for the switching section 3.

The receiver 6 can include e.g. members formed from a piezoelectric material and driving electrodes as in the piezoelectric section 101. However, the embodiment is not limited thereto. It is possible to appropriately select a configuration capable of generating an electrical signal in response to mechanical displacement.

In the foreign object detection device 1a, the generated reflection wave is received by the receiver 6, and converted to an electrical signal by the receiver 6.

This electrical signal based on the reflection wave is inputted to the detection section 5. Similarly to that described above, the presence or absence of a bubble B and the size of a bubble B are detected.

The detection of the presence or absence of a bubble B and the detection of the size of a bubble B can be made similar to those described above, and hence the detailed description thereof is omitted.

The foreign object detection device 1a according to this embodiment can achieve effects similar to those of the foreign object detection device 1 described above. Furthermore, because the switching section 3 can be omitted, the configuration can be simplified.

The operation of the droplet discharging device 100a can be made similar to that of the droplet discharging device 100 described above, and hence the detailed description thereof is omitted.

The foregoing has illustrated the case where the piezoelectric section 101 doubles as a transmitter and a receiver of the foreign object detection device 1, and the case where the piezoelectric section 101 doubles as a transmitter of the foreign object detection device 1a. However, the embodiments are not limited thereto. For instance, the piezoelectric section 101 can double as a receiver of the foreign object detection device. Alternatively, the piezoelectric section 101 and a transmitter and a receiver of the foreign object detection device can be provided separately. In the droplet discharging device of the thermal type, it is also possible to provide only a receiver of the foreign object detection device. In this case, the receiver is preferably configured as a piezoelectric section as described above.

Third Embodiment

Next, a foreign object detection method according to a third embodiment is illustrated.

Figure 6:
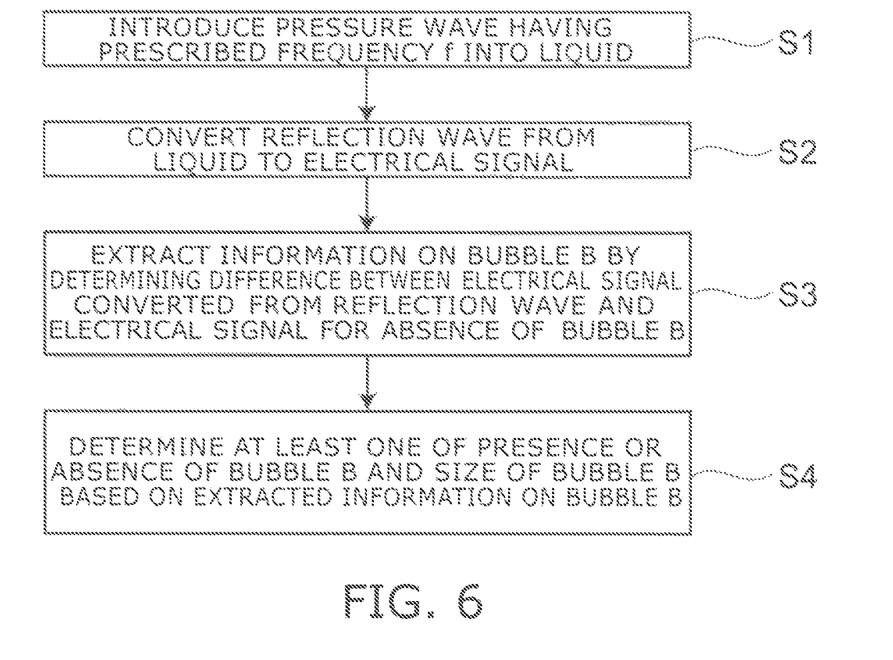
FIG. 6 is a flow chart for illustrating a foreign object detection method according to the third embodiment.

FIG. 6 is a flow chart for illustrating a foreign object detection method according to the third embodiment. In the following description, the case where the foreign object is a bubble B is taken as an example.

First, a pressure wave having a prescribed frequency f is introduced into the liquid (step S1).

In this case, the frequency f can be set to satisfy Equation (3). Furthermore, the frequency f can be set to satisfy Equation (4) as well.

In the case where a plurality of signal generators depending on the frequency range and a switching section for the frequency range are provided, the frequency range is switched so as to be able to generate an electrical signal having an appropriate frequency f.

Next, the reflection wave from the liquid is converted to an electrical signal (step S2).

Next, the difference between the electrical signal converted from the reflection wave and the electrical signal for the absence of a bubble B is determined to extract information on a bubble B (step S3).

Next, based on the extracted information on a bubble B, at least one of the presence or absence of a bubble B and the size of a bubble B is determined (step S4).

Here, the size of a bubble B can be determined similarly to that described above. For instance, the size of a foreign object can be detected based on the square of the difference between the electrical signal including the information on a bubble B and the information on the state of the absence of a bubble B.

Alternatively, for instance, the scattering cross-sectional area $\sigma sc$ is determined by Equations (1) and (2). Then, the radius dimension of a bubble B can be determined from the previously determined relationship between the radius dimension of a bubble B and the scattering cross-sectional area $\sigma sc$ (see e.g. FIG. 4).

Here, the content of each step can be made similar to that described above, and hence the detailed description thereof is omitted.

In the foregoing, the case of determining the presence or absence of a bubble B has been illustrated. However, it is also possible to determine the presence or absence of dust or other solid foreign object.

Furthermore, the case of determining the size of a bubble B has been illustrated. However, it is possible to determine the size of a foreign object undergoing volume change by pressure change.

The foreign object detection method according to this embodiment can accurately detect a bubble B or other foreign object even in a small region such as the liquid chamber 102a. Furthermore, the size of a bubble B or other foreign object can be determined with high accuracy. Thus, the prevention of trouble and the improvement of productivity can be achieved with higher reliability.

Fourth Embodiment

Next, a droplet discharging method according to a fourth embodiment is illustrated.

Figure 7:
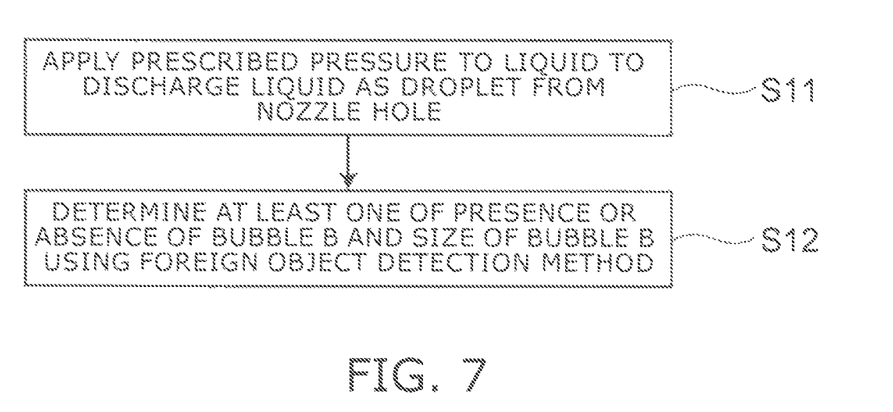
FIG. 7 is a flow chart for illustrating a droplet discharging method according to the fourth embodiment.

FIG. 7 is a flow chart for illustrating a droplet discharging method according to the fourth embodiment. In the following description, the case where the foreign object is a bubble B is taken as an example.

First, a prescribed pressure is applied to the liquid to discharge the liquid as a droplet from the nozzle hole (step S11).

Next, by using the foreign object detection method described above, at least one of the presence or absence of a bubble B and the size of a bubble B is determined (step S12).

In this case, for instance, the foreign object detection method can be performed successively or regularly.

If there is a bubble B larger than a prescribed threshold, a maintenance operation for suspending the discharge operation and ejecting the bubble B from the liquid can be performed.

In this case, alternatively, if the size of the bubble B is less than a prescribed threshold, the discharge operation can be continued. If the size of the bubble B is equal to or more than the prescribed threshold, a maintenance operation for suspending the discharge operation and ejecting the bubble B from the liquid can be performed.

The droplet discharging method according to this embodiment can prevent the occurrence of trouble and improve the productivity.

The embodiments illustrated above can realize a foreign object detection device, a foreign object detection method, a droplet discharging device, and a droplet discharging method capable of accurately detecting a foreign object.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

For instance, the shape, dimension, material, arrangement, number and the like of the components included in e.g. the foreign object detection device 1, the foreign object detection device 1a, the droplet discharging device 100, and the droplet discharging device 100a are not limited to those illustrated, but can be suitably modified.

What is claimed is:

1. A foreign object detection device comprising:
a signal generator configured to generate an electrical signal;
a transmitter configured to convert the electrical signal from the signal generator and to generate a pressure wave in a liquid;
a receiver configured to receive a reflection wave from the liquid and to convert it to an electrical signal;
a storage section configured to store information on a state of absence of a foreign object in the liquid; and
a detection section configured to detect at least one of presence or absence of the foreign object and size of the foreign object based on difference between the electrical signal converted from the reflection wave and an electrical signal based on the stored information, wherein
the signal generator generates the electrical signal having a frequency satisfying an equation given by $$f \approx \frac{1}{2\pi Ro} \sqrt{\frac{3\gamma Po}{\rho}}$$

where f is the frequency, Ro is maximum bubble size, Po is equilibrium pressure of the liquid, $\rho$ is density of the liquid, and $\gamma$ is specific heat ratio.

2. The device according to claim 1, wherein the detection section detects the size of the foreign object based on square of the difference between the electrical signal converted from the reflection wave and the electrical signal based on the stored information.

3. The device according to claim 1, wherein the detection section determines a scattering cross-sectional area based on the difference between the electrical signal converted from the reflection wave and the electrical signal based on the stored information, and detects the size of the foreign object from a previously determined relationship between the size of the foreign object and the scattering cross-sectional area.

4. The device according to claim 1, wherein the transmitter includes a piezoelectric material and generates in the liquid the pressure wave corresponding to the frequency of the electrical signal from the signal generator.

5. The device according to claim 1, wherein the receiver includes a piezoelectric material and generates the electrical signal corresponding to the reflection wave from the liquid.

6. The device according to claim 1, further comprising:
a switching section configured to switch between the electrical signal from the signal generator and the electrical signal from the receiver.

7. The device according to claim 1, further comprising:
a container configured to contain the liquid,
wherein the container has an equivalent diameter dimension satisfying an equation given by

[Equation 7]

$$d \le \frac{120}{f}$$

where f is frequency, and d is the equivalent diameter dimension of the container.

8. A droplet discharging device comprising:
a nozzle body including a liquid chamber;
a pressurizer provided on the nozzle body and configured to pressurize a liquid in the liquid chamber;
a nozzle section provided on the nozzle body and including a nozzle hole; and
the foreign object detection device according to claim 1.

9. The device according to claim 8, wherein the pressurizer doubles as at least one of the transmitter and the receiver provided in the foreign object detection device.

10. The device according to claim 8, wherein the pressurizer pressurizes the liquid in the liquid chamber based on the electrical signal from the signal generator provided in the foreign object detection device.

11. The device according to claim 8, wherein the liquid chamber has an equivalent diameter dimension satisfying an equation given by

[Equation 8]

$$d \le \frac{120}{f}$$

where d is the equivalent diameter dimension of the liquid chamber, and f is frequency.

12. A foreign object detection method comprising:
introducing a pressure wave having a prescribed frequency into a liquid;
converting a reflection wave from the liquid to an electrical signal;
extracting information on a foreign object by determining difference between the electrical signal converted from the reflection wave and an electrical signal for absence of the foreign object; and
determining at least one of presence or absence of the foreign object and size of the foreign object based on the extracted information on the foreign object, wherein
the introducing the pressure wave into the liquid includes introducing into the liquid the pressure wave having a frequency satisfying an equation given by $$f \approx \frac{1}{2\pi Ro} \sqrt{\frac{3\gamma Po}{\rho}}$$

where f is the frequency, Ro is maximum bubble size, Po is equilibrium pressure of the liquid, $\rho$ is density of the liquid, and $\gamma$ is specific heat ratio.

13. The method according to claim 12, wherein the size of the foreign object is determined based on square of the difference between the electrical signal converted from the reflection wave and the electrical signal for absence of the foreign object.

14. The method according to claim 12, wherein in determining the size of the foreign object, a scattering cross-sectional area is determined based on the difference between the electrical signal converted from the reflection wave and the electrical signal for absence of the foreign object, and the size of the foreign object is detected from a previously determined relationship between the size of the foreign object and the scattering cross-sectional area.

15. The method according to claim 12, wherein the introducing the pressure wave into the liquid includes introducing into the liquid the pressure wave having a frequency satisfying an equation given by

[Equation 10]

$$f \le \frac{120}{d}$$

where f is the frequency, and d is equivalent diameter dimension of a component containing the liquid.

16. A droplet discharging method comprising:
applying a prescribed pressure to a liquid and discharging the liquid as a droplet from a nozzle hole; and
determining at least one of presence or absence of a foreign object and size of the foreign object by using the foreign object detection method according to claim 12.

17. The method according to claim 16, further comprising:
making determination on occurrence of discharge anomaly based on the determined size of the foreign object.

18. The method according to claim 17, wherein in the making determination on occurrence of discharge anomaly, if it is determined that there is danger of the occurrence of discharge anomaly due to presence of the foreign object larger than a prescribed threshold, the foreign object larger than the prescribed threshold is ejected with the liquid from the nozzle hole.

* * * * *